US009470684B2

(12) United States Patent
Buss et al.

(10) Patent No.: US 9,470,684 B2
(45) Date of Patent: Oct. 18, 2016

(54) OUTER MEMBRANE PROTEIN 18 AS A DIAGNOSTIC MARKER FOR CAMPYLOBACTER

(71) Applicant: TECHLAB, INC., Blacksburg, VA (US)

(72) Inventors: Janice E. Buss, Dublin, VA (US); David M. Lyerly, Radford, VA (US); Tracy D. Wilkins, Riner, VA (US)

(73) Assignee: TECHLAB, INC., Blacksburg, VA (US)

( * ) Notice: Subject to any disclaimer, the term of this patent is extended or adjusted under 35 U.S.C. 154(b) by 0 days.

(21) Appl. No.: 14/451,843

(22) Filed: Aug. 5, 2014

(65) Prior Publication Data
US 2015/0044697 A1 Feb. 12, 2015

Related U.S. Application Data

(60) Provisional application No. 61/862,787, filed on Aug. 6, 2013.

(51) Int. Cl.
*G01N 33/569* (2006.01)
(52) U.S. Cl.
CPC .................. *G01N 33/56922* (2013.01)
(58) Field of Classification Search
None
See application file for complete search history.

(56) References Cited

U.S. PATENT DOCUMENTS

| 4,942,126 | A | 7/1990 | Slifkin | |
|---|---|---|---|---|
| 6,824,975 | B2 * | 11/2004 | Hubscher | G01N 33/558 422/417 |
| 8,961,990 | B2 * | 2/2015 | Hargis | A61K 39/105 424/190.1 |
| 2007/0128183 | A1 * | 6/2007 | Meinke | C07K 14/205 424/130.1 |
| 2013/0084304 | A1 * | 4/2013 | Hargis | A61K 39/105 424/190.1 |
| 2015/0030624 | A1 * | 1/2015 | Armstrong | A61K 39/105 424/190.1 |
| 2015/0044697 | A1 * | 2/2015 | Buss | G01N 33/56922 435/7.32 |
| 2015/0044698 | A1 * | 2/2015 | Buss | G01N 33/56922 435/7.32 |
| 2015/0190496 | A1 * | 7/2015 | Hargis | A61K 39/105 424/190.1 |

FOREIGN PATENT DOCUMENTS

| CN | 103941018 A * | 7/2014 |
| WO | WO 2005/103073 A2 * | 11/2005 |
| WO | WO 2011/156619 A2 * | 12/2011 |
| WO | 2013116639 | 8/2013 |
| WO | WO 2013/116639 A1 * | 8/2013 |
| WO | WO 2015/021125 A1 * | 2/2015 |

OTHER PUBLICATIONS

Zautner et al, Eur J Clin Microbiol Infect Dis (2014) 33:1019-1027.*
Corso et al, International Journal of Medical Microbiology, (Sep. 2011) vol. 301, Supp. Suppl. 1, pp. 29. Abstract Number: GIP01. Meeting Info: 63. Jahrestagung der Deutschen Gesellschaft fur Hygiene and Mikrobiologie, DGHM. Essen, Germany. Sep. 25, 2011-Sep. 28, 2011 (abstract only).*
Corso et al, Eurpoean J. Microbiology and Immunology, 2011, 1:86-94.*
International Search Report with Written Opinion dated Dec. 11, 2014 in Application No. PCT/US2014/049898, 12 pages.
Schmidt-Ott et al. "Improved serodiagnosis of Campylobacter jejuni infections using recombinant antigens," J Med Microbiol. Aug. 8, 2005, vol. 54, Pt. 8, pp. 761-767, entire document.
Bessede, E. A., 2011 "New Methods for Detection of Campylobacters in Stool Samples in Comparison to Culture." Journal of Clinical Microbiology, 49:941-944.
Bullman, S.J., 2012 "Molecular-based detection of non-culturable and emerging campylobacteria in patients presenting with gastoenteritis." Epidemiology & Infection, 140:684-688.
Burnens, A.U., 1995 "Identification and characterization of an immunogenic outer membrane protein of Campylobacter jejuni" Journal of Clinical Microbiology, 33:2826-32.
Cascales, E.A., 2002 "Pal Lipoprotein of *Escherichia coli* Plays a Major Role in Outer Membrane Integrity." Journal of Bacteriology, 184:754-759.
Couturier, B.A., 2013 "Detection of non *jejuni* and *-coli Campylobacter* Species from Stool Specimens with an Immunochromatographic Antigen Detection Assay." Journal of Clinical Microbiology, 51:1935-1937.
Couturier, B.A., 2012; Association of Campylobacter upsaliensis with Persistent Bloody Diarrhea. Journal of Clinical Microbiology, 50:3792-3794.
Fouts D.E., 2005 "Major Structural Differences and Novel Potential Virulence Mechanisms from the Genomes of Multiple *Campylobacter* Species." PLoS Biol, 3:e15.
Friedman, C.R., 2004 "Risk factors for sporadic Campylobacter infection in the United States: A case-control study in FoodNet sites." Clinical Infectious Diseases, 38:S285-96.

(Continued)

*Primary Examiner* — Nita M Minnifield
(74) *Attorney, Agent, or Firm* — Shook, Hardy & Bacon L.L.P.

(57) ABSTRACT

Accurate and fast detection of the presence of *Campylobacter* disease is important for the proper treatment of patients with *Campylobacter* infection. Present tests depend upon culture of viable bacteria and identification by microscopy, which requires care, skill, and two or more days for conclusive results. The current invention improves the ease of use and overcomes the limitations of loss of viability and delay inherent in *Campylobacter* bacterial culture and provides a more rapid alternative for the identification and diagnosis of *Campylobacter* and campylobacteriosis. The invention provides a new method of detecting *Campylobacter* by utilizing an outer membrane protein (OMP 18) to develop antibodies for use in immunoassays of bacterial cultures or human fecal samples.

20 Claims, 4 Drawing Sheets

(56) References Cited

OTHER PUBLICATIONS

Guerrant, R.L., 2001 "Practice Guidelines for the Management of Infectious Diarrhea." Clinical Infectious Diseases, 32:331-351.
Hall, G., M.D. 2005 "Estimating foodborne gastroenteritis" Australia. Emerg In-fect Dis 11:1257-1264.
Hatchette, T.F., 2011 "Infectious diarrhea: When to test and when to treat." Canadian Medical Association Journal, 183:339-344.
Hurd, S., 2012 "Clinical Laboratory Practices for the Isolation and Identification of Campylobacter in Foodborne Diseases Active Surveillance Network (FoodNet) Sites: Baseline Information for Understanding Changes in Surveillance Data." Clinical Infectious Diseases, 54:S440-S445.
Iovine, N.M., 2013 "Resistance Mechanisms in Campylobacter jejuni." Virulence, 4:230-240.
Kendall, M.E., 2012 "Travel-Associated Enteric Infections Diagnosed After Return to the United States" Foodborne Diseases Active Surveillance Network (FoodNet), 2004-2009; Clinical Infectious Diseases, 54:S480-S487.
Kirkpatrick, B. D., 2011 "Update on human Campylobacter jejuni infections" Curr Opin Gastoenteral, 27:1-7.
Konkel, M.E., 1996 "Cloning, sequencing, and expression of a gene from Campylobacter jejuni encoding a protein (Omp18) with similarity to peptidoglycan-associated lipoproteins." Infection and Immunity, 64:1850-3.
Kuhn, K.G., 2012 "Detection of antibodies to Campylobacter in humans using enzyme-linked immunosorbent assays: a review of the literature." Diagn Microbiol Infect Dis, 74:113-118.
Lastovica, A.J., 2000 "Efficient Isolation of Campylobacteria from Stools." Journal of Clinical Microbiology, 38:2798-2799.
Man, S.M., 2011 "The clinical importance of emerging *Campylobacter* species." Nat Rev Gastoenterol Hepatol, 8:669_685.
Pawelec, D.P., 2000 "Genetic diversity of the Campylobacter genes coding immuniodominant proteins." FEMS Microbiology Letters, 185:43-49.
Ruiz-Palacios, G.M. 2007 "The health burden of Campylobacter infection and the impact of antimicrobial resistance: playing chicken." Clin Infect Dis, 44:701-703.
Young, K.T., 2007 "Campylobacter jejuni: molecular biology and pathogenesis." Nature Reviews Microbiology, 5:665-679.
International Preliminary Report on Patentability Dated Feb. 18, 2016 for PCT Patent Application No. PCT/US22014/049898, 9 Pages.
Non-Final Office Action dated Sep. 24, 2015 in U.S. Appl. No. 14/451,847, 9 pages.

* cited by examiner

MKKILFTSIAALAVVISG <sup>19</sup>CSTKSTSVSGDSSVDSNRGSGGSDGWDIDSKISQLNDTLNK
VYFDFDKFNIRPDMQNVVSTNANIFNTEVSGVSITVEGNCDEWGTDEYNQALGLKRAKAVK
EALIAKGVNADRIAVKSYGETNPVCTEKTKACDAQNRRAEFKLSR

SEQUENCE LISTING

<160> NUMBER OF SEQ ID NOS: 1

<210> SEQ ID NO 1
<211> LENGTH: 165
<212> TYPE: PRT
<213> ORGANISM: Campylobacter jejuni ATCC 33560

<400> SEQUENCE: 1

-continued

```
Met Lys Lys Ile Leu Phe Thr Ser Ile Ala Ala Leu Ala Val Val Ile
1               5               10                  15

Ser Gly Cys Ser Thr Lys Ser Thr Ser Val Ser Gly Asp Ser Ser Val
                20              25              30

Asp Ser Asn Arg Gly Ser Gly Gly Ser Asp Gly Trp Asp Ile Asp Ser
        35              40                  45

Lys Ile Ser Gln Leu Asn Asp Thr Leu Asn Lys Val Tyr Phe Asp Phe
    50              55              60

Asp Lys Phe Asn Ile Arg Pro Asp Met Gln Asn Val Val Ser Thr Asn
65              70              75                      80

Ala Asn Ile Phe Asn Thr Glu Val Ser Gly Val Ser Ile Thr Val Glu
            85              90              95

Gly Asn Cys Asp Glu Trp Gly Thr Asp Glu Tyr Asn Gln Ala Leu Gly
            100             105             110

Leu Lys Arg Ala Lys Ala Val Lys Glu Ala Leu Ile Ala Lys Gly Val
        115             120             125

Asn Ala Asp Arg Ile Ala Val Lys Ser Tyr Gly Glu Thr Asn Pro Val
    130             135             140

Cys Thr Glu Lys Thr Lys Ala Cys Asp Ala Gln Asn Arg Arg Ala Glu
145             150             155             160

Phe Lys Leu Ser Arg
                165
```

OUTER MEMBRANE PROTEIN 18 AS A DIAGNOSTIC MARKER FOR CAMPYLOBACTER

CROSS REFERENCE TO RELATED APPLICATIONS

This application claims priority from U.S. Provisional Application No. 61/862,787, filed Aug. 6, 2013, entitled "Outer Membrane Protein 18 (CJ0113) as a Diagnostic Marker for *Campylobacter*," the entire contents of which are herein incorporated by reference.

BRIEF SUMMARY

The present invention provides a method to develop immunoassays for the detection of *Campylobacter*. The invention includes a method for use of a recombinant form of a *Campylobacter* outer membrane protein (OMP18) as an antigen and use of antibodies produced to the antigen in antibody-based diagnostic assays for *Campylobacter*. The object of the present invention is to overcome the difficulty of the prior art, which is identification or diagnosis of *Campylobacter* based on the culture of the bacteria.

SEQUENCE LISTING

A text file in compliance with ASCII and having a ".txt" extension has been electronically submitted via EFS-Web. The text file named "Sequence Listing" was created on Aug. 1, 2014, and is 1.78 KB. The text file is expressly incorporated by reference herein in its entirety.

BACKGROUND

The Center for Disease Control estimates that, as of 2011, almost 48 million people in the USA experience some form of food-borne illness every year. Of these, 128,000 are hospitalized and 3000 die. Worldwide, *Campylobacter* species are the most common cause of bacterial gastroenteritis, with 400-500 million cases of diarrhea each year. Infants in developing countries are at even greater risk, as are travelers to those countries. *Campylobacter*—associated gastroenteritis is estimated to affect nearly 1 million people a year in the USA. In approximately 1 in 1000 cases, *Campylobacter jejuni* is closely linked to the subsequent development of Guillian-Barre Syndrome, an acute, auto-immune paralysis. *C. jejuni* infection has also been associated with reactive arthritis in both children and adults.

In addition to *Campylobacter* spp., other common causes of bacterial food-borne gastroenteritis are enteropathogenic *Escherichia coli*, and *Salmonella* spp.; norovirus is a significant viral cause of food-borne disease. Although many cases of "food poisoning" self-resolve without the need for medical treatment, infants and the elderly are at higher risk for dehydration and more serious complications.

When individuals with severe symptoms of gastroenteritis seek medical help, the clinician is faced with multiple possible causes that can present with similar clinical features (e.g., diarrhea, nausea, vomiting, fever, abdominal pain) but that require very different treatment. For viruses, use of antibiotics is ineffective and can contribute to development of antibiotic resistance in bacteria. Ineffective empirical treatment can release selective pressure on resident resistant bacteria and convert non-symptomatic infection into illness. Treatment of enteropathogenic *E. coli* with antibiotics is contraindicated, as this may actually increase the chances of the patient experiencing hemolytic uremic syndrome (HUS). Antibiotic treatment of *Salmonella*-caused gastroenteritis may prolong the carrier state and is associated with relapse. Conversely, erythromycin treatment of *Campylobacter* infection may shorten illness and the time during which bacteria are shed, but only if the antibiotic is begun within 4 days of the onset of symptoms. Post-infectious irritable bowel syndrome has been associated with a longer duration of untreated infection. Identifying, without delay, which organism may be causing the gastroenteritis is important for diagnosis and selection of the appropriate treatment.

For *Campylobacter*, the current standard for identification is bacterial culture followed by microscopic examination of the organisms. Although this traditional method is straightforward, it has three major limitations. First, pathogenic species of *Campylobacter* are microaerophilic or strictly anaerobic, so that exposure of culture or stool to environmental oxygen conditions leads to death or inactivation of the bacteria. Thus, during transport or storage of specimens the number of viable organisms can decrease, leading to potentially inaccurate culture results. Second, while the standard culture medium and microaerophilic incubation conditions have been improved for two common species, *Campylobacter jejuni* (Cj) and *Campylobacter coli* (Cc), other *Campylobacter* species such as *C. lari, C. upsaliensis, C. ureolyticus* and *C. hyointestinalis* have also been linked to human disease, but are more difficult to grow and require different culture media and anaerobic incubation that are not routinely available in clinical laboratories. As a result, illnesses caused by these more fastidious, but never-the-less pathogenic organisms, are likely to go unrecognized and unreported. Third, even with appropriate culture conditions, each of these species is slow-growing, requiring from 48-72 hours (e.g., Cj or Cc) up to 7 days before reaching a point where the culture can safely be reported out as negative. Prolonged culture lengths are particularly true in the food safety industry, in which rinses of poultry carcasses or samples of raw milk (the most commonly identified sources of *Campylobacter* illnesses) are sampled for surveillance of sanitation measures or during outbreaks. Such delays can leave the clinician in a quandary and the patient with non-specific, ineffective, or even inappropriate treatment.

To provide a more rapid alternative to growth of cultures and microscopy for the identification and diagnosis of *Campylobacter* and campylobacteriosis, the present invention utilizes an outer membrane protein (OMP 18) as a biomarker for use in immunoassays of bacterial cultures or human fecal samples. The fecal samples used in the present invention may be unpreserved or preserved.

OMP 18 is an 18 kilodalton protein found in the outer membrane of many *Campylobacter* species. The amino acid sequence of OMP 18 is partially homologous to a similar protein, PAL in *E. coli*. The *E. coli* PAL protein is a peptidoglycan-associated lipoprotein, and the *Campylobacter* OMP18 is predicted to share these properties.

Several properties of OMP18 make it a good candidate for a diagnostic marker. Outer membrane proteins are typically subject to significant variation even among strains of the same species. The flagellin protein (FlaA), major outer membrane protein (MOMP/PorA) and fibronectin-binding protein (CadF) show large variability even between *Campylobacter jejuni* strains. However, from the genomic sequences of various strains of Cj that are currently available, the amino acids of OMP 18 (*C jejuni* subsp *jejuni*, ATTC 33560; GenBank: EIB41509.1) (FIG. 1) are completely identical among 51 strains of *C. jejuni* and 93% identical to the OMP18 protein of *C. coli*. OMP 18 thus provides a potential immunogen that is well-conserved among many strains of Cj and Cc. Conversely, OMP 18 bears little similarity to outer membrane proteins of *Campylobacter* species that are non-pathogenic or that are not clearly associated with human illness. Additionally, as a proposed antigen, OMP 18 has been shown to be highly immunogenic, a requirement for robust immunoassays. Serum from individuals that have had confirmed campylobacteriosis contains antibodies that recognize OMP 18 in immunoblots of bacterial cultures.

The present invention is directed towards improving ease of use and overcoming the limitations of delay inherent in *Campylobacter* bacterial culture. As previously stated, the current standard for identification of *Campylobacter* is through culturing and microscopy, which has several limitations, such as decreased viability with exposure to aerobic conditions. In contrast, in an embodiment of the present invention, a new method of detecting *Campylobacter* in stool samples using antibodies to OMP18 in immunoassays is provided. Antibody-based tests, such as Enzyme-linked immunosorbent assays (ELISAs) and lateral flow tests, are rapid and cost-effective tests for detection of pathogen-specific antigens. Furthermore, this new method allows for the identification of *Campylobacter* in aerobic conditions, without culturing. Thus, the identification of *Campylobacter* can take place even when the sample is not alive. This is beneficial, for example, if a sample is brought into the lab under prolonged aerobic conditions. We propose to use OMP18 as an antigen, and antibodies developed using OMP18, for the detection of *Campylobacter* in stool.

BRIEF DESCRIPTION OF THE DRAWINGS

Illustrative embodiments of the present invention are described in detail below with reference to the attached drawing figures, wherein.

DETAILED DESCRIPTION

Figures 1, 2, 3:
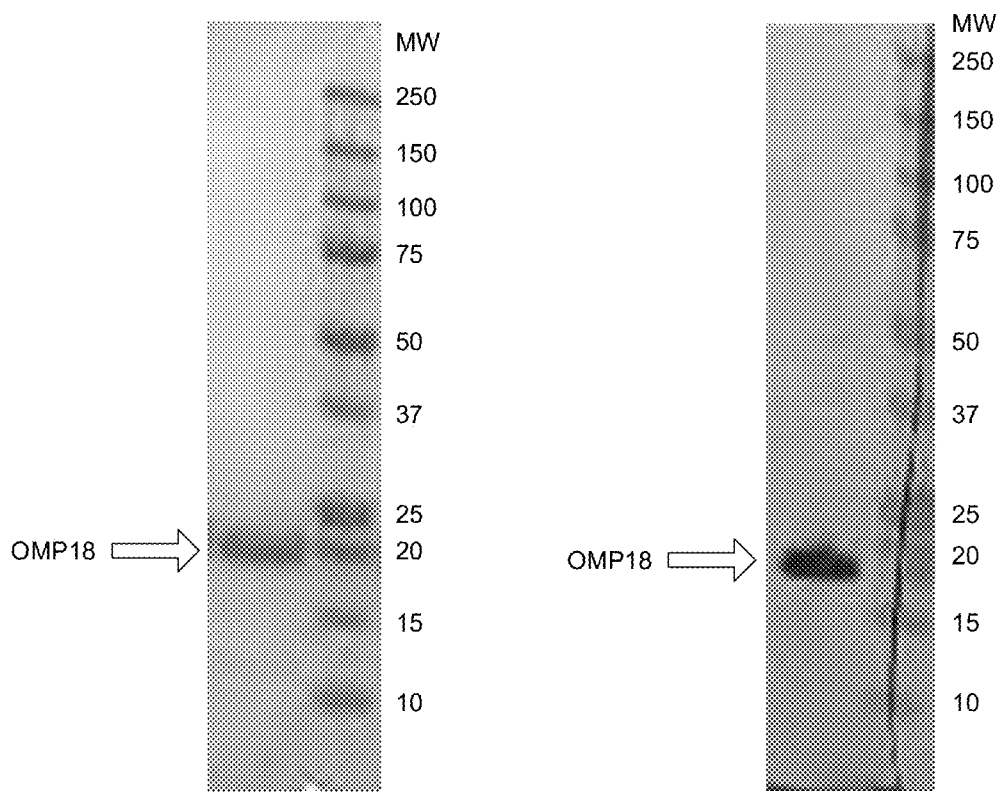
FIG. 1 depicts the amino acid sequence of OMP18 from *Campylobacter jejuni* subspecies *jejuni* strain ATTC 33560; GenBank: EIB41509.1.
FIG. 2 depicts a Coomassie Blue-stained SDS-polyacrylamide gel of recombinant OMP18, which was used as antigen.
FIG. 3 depicts an immunoblot in which proteins from *C. jejuni* bacteria were separated by SDS-polyacrylamide gel electrophoresis, transferred to a membrane, and incubated with HRP-conjugated, affinity-purified anti-OMP18.

Embodiments of the present invention may be embodied as, among other things, a method, a device, and the like for testing fecal samples and identifying the presence of the Outer Membrane Protein 18 (OMP18).

Accordingly, in one aspect, the present invention is directed to a method for testing a fecal sample from a person. The method includes obtaining a fecal sample from the person, determining whether Outer Membrane Protein 18 (OMP18) is present in the fecal sample, and upon determining OMP18 is present in the fecal sample, diagnosing the person with *Campylobacter* infection.

In another aspect, the present invention is directed to a method for testing a bacterial culture that is derived from a fecal sample from a person. The method includes obtaining a fecal sample from the person, preparing and growing *Campylobacter* bacteria from the sample by standard methods, determining whether OMP18 is present in the bacterial culture sample, and upon determining OMP18 is present in the bacterial culture sample, diagnosing the person with *Campylobacter* infection.

In yet another aspect, the present invention is directed to a device to test a fecal sample for the presence of OMP18 to be utilized to diagnose a person with *Campylobacter* infection. The device comprises a receiving portion to receive a fecal sample from a person, and a testing portion to detect OMP 18 in the fecal sample to be utilized to diagnose a person with *Campylobacter* disease.

In yet another embodiment, the present invention is directed to a method for detecting *Campylobacter* in a fecal sample from a person. The method includes obtaining the fecal sample from the person, determining the presence of OMP18 in the fecal sample by contacting said fecal sample with a purified antibody that reacts specifically with Omp18 or reactive fragment thereof under suitable conditions to form a complex of said Omp18 or reactive fragment thereof and the purified antibody, wherein the purified antibody specifically reacts with Omp18 amino acid sequence of SEQ. ID NO: 1 or any amino acid sequence having at least 70% identity with SEQ. ID NO:1, and detecting the presence of said complex, wherein the presence of said complex results in diagnosing the person with *Campylobacter* infection.

In an additional embodiment, the present invention is directed to a method for detecting *Campylobacter* in a bacterial culture that is derived from a fecal sample from a person. The method includes obtaining the fecal sample from the person, preparing and growing *Campylobacter* bacteria from the fecal sample, determining the presence of OMP 18 in the bacterial culture by contacting said bacterial culture with a purified antibody that reacts specifically with Omp18 or reactive fragment thereof under suitable conditions to form a complex, of said Omp18 or reactive fragment thereof and the purified antibody, wherein the purified antibody specifically reacts with Omp18 amino acid sequence of SEQ. ID NO:1 or any amino acid sequence having at least 70% identity with SEQ. ID NO:1, and detecting the presence of said complex, wherein the presence of said complex indicates a diagnosis of the person with *Campylobacter* infection.

The following are examples of procedures which have been utilized to establish the preferred assays according to the present invention. The following examples are merely exemplary and not presented by way of limitation.

Example 1

DNA encoding amino acids 29-165 of OMP 18 (*C. jejuni* subspecies *jejuni*, strain ATTC 33560; GenBank: EIB41509.1) was synthesized commercially and expressed in *E. coli*. Recombinant Omp18 (either untagged or synthesized so that it contained an affinity tag) was purified from the *E. coli* lysates by chromatography (as illustrated in FIG. 2) and used as the antigen to make polyclonal antibodies in goats. The OMP18 protein was also coupled to NHS-Sepharose for use in affinity-based purifications of the resulting antibodies. The ability of the purified antibodies to bind specifically to the native form of the OMP18 protein when the OMP18 is present in a lysate of *Campylobacter jejuni* bacteria was tested and confirmed by immunoblotting (as illustrated in FIG. 3).

Specifically, FIG. 2 illustrates a preparation of recombinant OMP18 that had been purified by chromatography, was separated by SDS-polyacrylamide gel electrophoresis and stained with Coomassie Blue. The right hand lane displays molecular weight markers. The arrow points to OMP18 at the appropriate 18 kilodalton size. The lack of other significant protein bands indicates that the preparation is highly purified.

FIG. 3 illustrates a sample of *Campylobacter jejuni* bacteria that was separated by SDS-polyacrylamide gel electrophoresis, transferred to a membrane, and incubated with HRP-conjugated anti-OMP18. The right hand lane displays molecular weight markers. The arrow points to OMP18. Among the thousands of proteins present on the immunoblots from the bacterial sample, only the native 18 kilodalton OMP18 protein was recognized by the purified anti-OMP18 antibodies.

Figure 4:
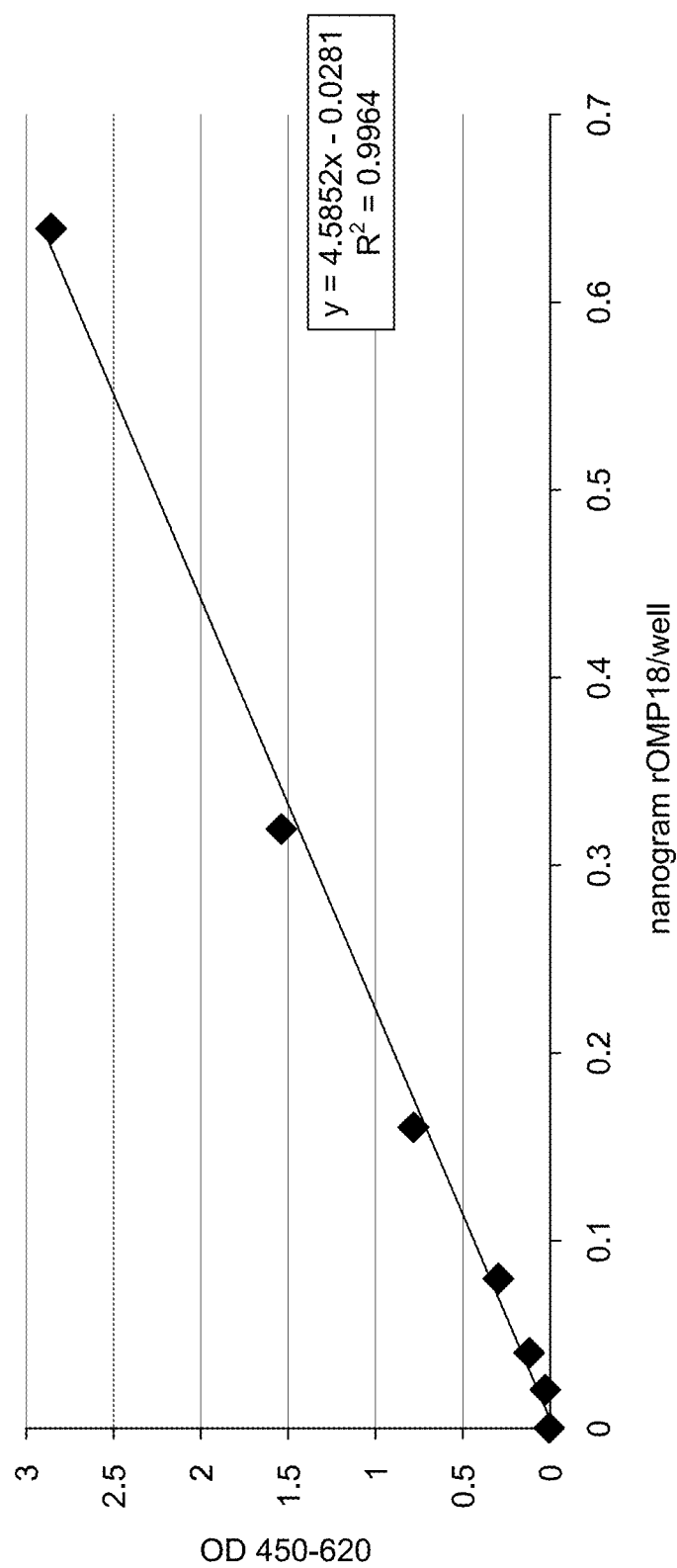
FIG. 4 depicts a graphical representation of a response curve of recombinant OMP18 on an anti-OMP18 ELISA.

An ELISA (enzyme-linked immunosorbent assay) was developed using polyclonal anti-OMP18 antibodies as capturing antibodies and horseradish peroxidase (HRP)-conjugated polyclonal anti-OMP18 antibodies as detection antibodies. The recombinant OMP18 antigen was tested on the ELISA and produced a response with an excellent fit ($R^2=0.99$) to a linear trend line as illustrated in FIG. 4. The ability of the assay to detect sub-nanogram amounts of OMP18 (<0.04 ng recombinant OMP18) confirms that the antibodies produced to the OMP18 antigen are highly sensitive.

Example 2

Twenty-eight human fecal samples that were positive and 198 that were negative by standard laboratory culture for *Campylobacter jejuni* and *Campylobacter coli* were tested using this anti-OMP18 ELISA. Samples were diluted five-fold, added to the ELISA wells, HRP-conjugated polyclonal Anti-OMP18 antibody added, and the plate incubated for 20 minutes at 37 degrees C. Wells were washed, standard HRP substrate added for 10 minutes, followed by a standard solution to stop the color development reaction. The cutoff of this ELISA was set as an absorbance of 0.080 by dual wavelength (OD450-620 nm) spectrometry. Twenty-six of the 28 culture-positive samples were positive on the anti-OMP ELISA, for a sensitivity of 93%. One hundred eighty-eight of the 198 culture-negative samples were negative on the anti-OMP ELISA, for a specificity of 95%. Table 1 below illustrates this result.

TABLE 1

|  |  | Culture Positive Total = 28 | Culture Negative Total = 198 |
|---|---|---|---|
| OMP18 ELISA Positive | Total = 36 | 26 | 10 |
| OMP18 ELISA Negative | Total = 190 | 2 | 188 |
|  |  | Sensitivity = 93% | Specificity = 95% |

Example 3

Figure 5:
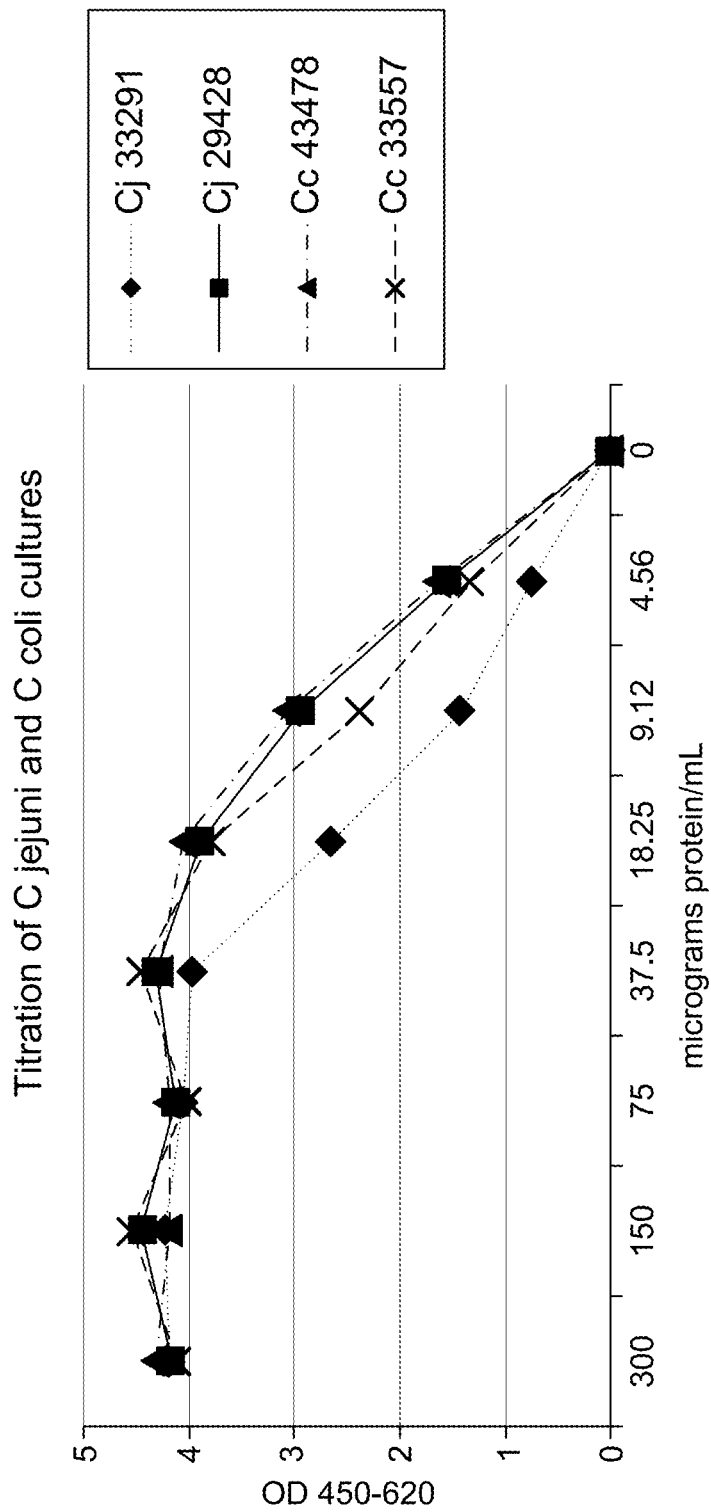
FIG. 5 depicts a graphical representation of a response curve of several strains of *Campylobacter jejuni* and *Campylobacter coli* on an anti-OMP18 ELISA.

The OMP18 ELISA can also be used to detect *Campylobacter jejuni* and *Campylobacter coli* from bacterial cultures. Using the ELISA assay described in Example 2, individual cultures of 2 strains of *Campylobacter jejuni*, and 2 strains of *Campylobacter coli* were tested. Bacterial cultures were scraped from agar growth plates (CAMPY CVA plates, Hardy Diagnostics) into phosphate-buffered saline (PBS). Protein concentrations of appropriate dilutions of the bacterial suspensions were determined using a commercial Coomassie Blue-based (Bradford) assay. Suspensions were adjusted to 3 mg protein/ml and, from a starting concentration of 300 micrograms protein per milliliter, one hundred microliters of serial two-fold dilutions of each bacterial suspension was added to wells of the ELISA plate. Incubation, development and reading of the plate were performed as in Example 2. FIG. 5 illustrates the results of titration of these *Campylobacter* cultures. Each of the four *Campylobacter* strains from bacterial culture was detected strongly by the OMP18 ELISA assay. Thus OMP18 can be used as a marker to detect multiple strains of *Campylobacter jejuni* or *Campylobacter coli*.

Example 4

Positive ELISA test results for OMP18 were also compared to known PCR markers that are specific to *Campylobacter*. The 28 fecal samples that were culture positive were further tested using in-house PCR assays that detect 16S ribosomal RNA of *C. jejuni* and *C. coli*, the hipO gene of *C. jejuni* and the CadF gene of *C. coli*. Of these 28 culture-positive samples, 26 were also PCR-positive, while 2 samples could not be confirmed as positive by PCR analysis as illustrated below in Table 2. These 26 samples were also positive for *Campylobacter* by the OMP18-based ELISA assay. The results confirm that the anti-OMP ELISA detects true positives accurately.

A subset of 107 of the 198 culture-negative samples were also tested using the PCR assay as illustrated in Table 2. All 107 of the negative fecal samples were also found to be negative by PCR. Among these 107 negative samples, 106 were indicated as negative and one was positive by the anti-OMP ELISA assay. This indicates that the anti-OMP ELISA can also distinguish negative samples with high accuracy.

The high degree of correlation between positive PCR results and positive ELISA results verified the validity of the ELISA assay for the presence of OMP18.

TABLE 2

|  |  | PCR Positive Total = 26 | PCR Negative Total = 107 |
|---|---|---|---|
| OMP18 ELISA Positive | Total = 24 | 23 | 1 |
| OMP18 ELISA Negative | Total = 109 | 3 | 106 |
|  |  | Sensitivity = 88% | Specificity = 99% |

Example 5

In addition to the OMP18 ELISA, a rapid enzyme-linked immunoassay (rapid EIA) using anti-OMP18 antibodies striped onto membranes and horseradish peroxidase (HRP)-conjugated anti-OMP18 antibodies as detection antibodies was developed. The recombinant OMP18 antigen was tested on the membrane-based rapid EIA and, similar to the OMP18 ELISA, could detect sub-nanogram amounts of OMP18 (<0.15 ng recombinant OMP18). The OMP18 EIA was used to test 37 human fecal samples that were *Campylobacter* positive by standard culture techniques, and 643 samples that were culture-negative. Samples were diluted five-fold, mixed with a drop of HRP-conjugated anti-OMP18 antibody, and added to the EIA membrane device. Devices were incubated for 15 minutes at room temperature, washed with 300 μL of buffer, one drop of the HRP-conjugated anti-OMP18 added, and incubation continued another 10 minutes. Visible detection of a blue-colored test line in the reaction window indicated a positive reaction for the presence of *Campylobacter* OMP18 in the sample. Of the 37 culture-positive specimens, the OMP18 rapid EIA detected 36, for a sensitivity of 97%. Among the 643 culture-negative specimens, the OMP18 rapid EIA detected 8 positives, and 635 negatives, for a specificity of 99%. Thus, anti-OMP18 can be used accurately in multiple detection formats.

TABLE 3

|  |  | Culture Positive Total = 37 | Culture Negative Total = 643 |
|---|---|---|---|
| OMP18 rapid EIA Positive | Total = 44 | 36 | 8 |
| OMP18 rapid EIA Negative | Total = 636 | 1 | 635 |
|  |  | Sensitivity = 97% | Specificity = 99% |

Example 6

Figure 6:
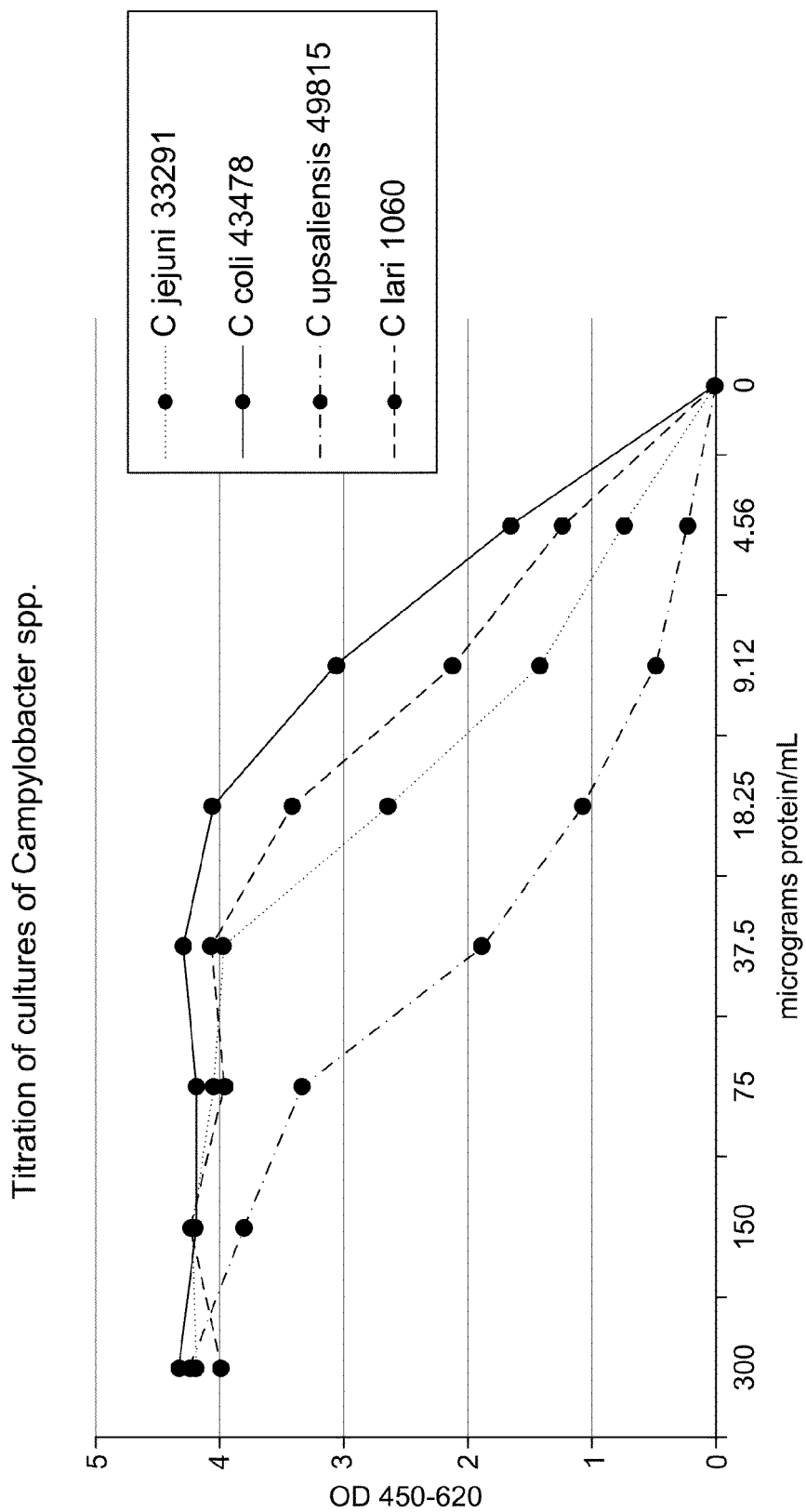
FIG. 6 shows a graphical representation of the response curve of the anti-OMP18 ELISA to bacterial cultures of four species of *Campylobacter*.

The OMP18 ELISA can also be used to detect OMP18 in *Campylobacter* species which are closely related to *C. jejuni* and in which the amino acid sequence of the species' OMP18 is homologous as illustrated in Table 4. Using the ELISA assay described in Example 2, individual cultures of *Campylobacter lari* and *Campylobacter upsaliensis* were tested. Bacterial cultures were grown on AnaeroGro Campy Selective Agar plates for 48-72 hours at 37 degrees C. in a microaerophilic atmosphere generated by CampyGen Sachets. Bacterial cultures were scraped from agar growth plates into phosphate-buffered saline (PBS). Protein concentrations of appropriate dilutions of the bacterial suspensions were determined using a commercial Coomassie Blue-based (Bradford) assay. Suspensions were adjusted to 3 mg protein/ml and, from a starting concentration of 300 micrograms protein per milliliter, one hundred microliters of serial two-fold dilutions of each bacterial suspension was added to wells of the ELISA plate. Incubation, development and reading of the plate were performed as in Example 2. FIG. 6 illustrates the results of titration of these *Campylobacter* cultures along with titrations of cultures of *C. jejuni* and *C. coli*. The two additional *Campylobacter* species from bacterial culture were detected strongly by the OMP18 ELISA assay. Thus OMP18 and antibodies to the protein can be used to detect multiple species of *Campylobacter*.

TABLE 4

| Species (strain) | Accession No. for OMP 18 | Amino Acid Identity to Cj |
|---|---|---|
| *Campylobacter jejuni* (81116) | YP_1781132.1 |  |
| *Campylobacter coli* (RM2228) | ZP_00367850.1 | 94% |
| *Campylobacter upsaliensis* (RM3195) | ZP_00371247.1 | 89% |
| *Campylobacter lari* (RM2100) | YP_002574815.1 | 71% |

Table 4 illustrates the results of alignment of the amino acid sequences of the OMP18 proteins of the four indicated *Campylobacter* species using the NCBI BLAST protein algorithm 2.2.29. The percent identity of the amino acids calculated by the algorithm are given in the table above.

In summary, the present invention provides OMP18 as a diagnostic marker for detecting *Campylobacter* in stool samples and bacterial cultures. The examples and embodiments of the present invention have been described in relation to particular embodiments which are intended in all respects to be illustrative rather than restrictive. Alternative embodiments will become apparent to those skilled in the art to which the present invention pertains without departing from its scope.

In its most basic form, the device of the invention comprises (1) a receiving portion to receive a fecal sample from a person and (2) a testing portion to detect the presence of OMP18 in the fecal sample, where the testing portion comprises a specific binding pair member that is specific for OMP18. Any additional components that permit the practice of the method of the invention may also be included in the device.

From the foregoing, it will be seen that this invention is one well adapted to attain all the ends and objects herein above set forth together with other advantages which are obvious and which are inherent to the method. It will be understood that certain features and sub-combinations are of utility and may be employed without reference to other features and sub-combinations. This is contemplated by and is within the scope of the claims.

What the invention claims is:

1. A method for testing a fecal sample from a person having symptoms associated with gastroenteritis, the method comprising:
    obtaining a fecal sample from the person having symptoms associated with gastroenteritis;
    using one or more antibodies against Outer Membrane Protein 18 (OMP18) to determine whether OMP18 is present in the fecal sample; and
    upon determining OMP18 is present in the fecal sample, diagnosing the person with *Campylobacter* infection.

2. The method of claim 1, wherein the one or more antibodies against OMP18 are raised against a full length sequence of a native OMP18 purified from at least one *Campylobacter* species.

3. The method of claim 1, wherein the one or more antibodies against OMP18 are raised against recombinant OMP18 expressed in bacteria, yeast, or mammalian cells.

4. The method of claim 1, wherein the one or more antibodies against OMP18 comprise one or more polyclonal antibodies that specifically recognize OMP18.

5. The method of claim 1, wherein the one or more antibodies against OMP18 are raised against one or more OMP18 proteins from one or more *Campylobacter* species.

6. The method of claim 1, wherein the presence of OMP18 is identified using lateral flow techniques and immunochemical reactions on a membrane or an enzyme-linked immunoassay.

7. The method of claim 6, wherein the one or more antibodies against OMP18 are raised against a full length sequence of a native OMP18 purified from at least one *Campylobacter* species.

8. The method of claim 6, wherein the one or more antibodies against OMP18 are raised against recombinant OMP18 expressed in bacterial, yeast, or mammalian cells.

9. The method of claim 6, wherein the one or more antibodies against OMP18 are raised against one or more OMP18 proteins from one or more *Campylobacter* species.

10. The method of claim 6, wherein the one or more antibodies comprise one or more polyclonal antibodies that specifically recognize OMP18.

11. The method of claim 1, wherein the one or more antibodies against OMP18 comprise one or more monoclonal antibodies that specifically recognize OMP18.

12. The method of claim 6, wherein the one or more antibodies against OMP18 comprise one or more monoclonal antibodies that specifically recognize OMP18.

13. The method of claim 1, wherein the one or more antibodies against OMP18 are raised against a protein having at least 70% identity with SEQ. ID NO:1 purified from at least one *Campylobacter* species.

14. The method of claim 6, wherein the one or more antibodies against OMP18 are raised against a protein having at least 70% identity with SEQ. ID NO:1 purified from at least one *Campylobacter* species.

15. The method of claim 1, wherein the one or more antibodies against OMP18 are raised against a protein having at least 89% identity with SEQ. ID NO:1 purified from at least one *Campylobacter* species.

16. The method of claim 6, wherein the one or more antibodies against OMP18 are raised against a protein having at least 89% identity with SEQ. ID NO:1 purified from at least one *Campylobacter* species.

17. The method of claim 1, wherein the one or more antibodies against OMP18 are raised against a protein having at least 94% identity with SEQ. ID NO:1 purified from at least one *Campylobacter* species.

18. The method of claim 6, wherein the one or more antibodies against OMP18 are raised against a protein having at least 94% identity with SEQ. ID NO:1 purified from at least one *Campylobacter* species.

19. The method of claim 5, wherein the one or more OMP18 proteins comprise at least two OMP18 proteins from different *Campylobacter* species, the at least two OMP18 proteins having amino acid sequences that are at least partly different from one another.

20. The method of claim 1, wherein the presence of OMP18 is identified using lateral flow techniques and immunochemical reactions on a membrane.

\* \* \* \* \*